US011959271B2

(12) United States Patent
Brown et al.

(10) Patent No.: US 11,959,271 B2
(45) Date of Patent: Apr. 16, 2024

(54) MICROBES FOR SPACE STRUCTURES

(71) Applicant: Raytheon BBN Technologies Corp., Cambridge, MA (US)

(72) Inventors: Michael D. Brown, Tiverton, RI (US); Helen G. Scott, Cambridge, MA (US); Miles T. Rogers, Watertown, MA (US); Benjamin J. Rosenthal, Newport, RI (US); Michael J. Nicoletti, Johnston, RI (US); James J. Stusse, Middletown, RI (US)

(73) Assignee: RAYTHEON BBN TECHNOLOGIES CORP., Cambridge, MA (US)

( * ) Notice: Subject to any disclaimer, the term of this patent is extended or adjusted under 35 U.S.C. 154(b) by 215 days.

(21) Appl. No.: 17/696,990

(22) Filed: Mar. 17, 2022

(65) Prior Publication Data
US 2022/0298780 A1    Sep. 22, 2022

Related U.S. Application Data

(60) Provisional application No. 63/162,794, filed on Mar. 18, 2021.

(51) Int. Cl.
*E04B 1/62* (2006.01)
*C04B 14/02* (2006.01)
(Continued)

(52) U.S. Cl.
CPC .............. *E04B 1/62* (2013.01); *C04B 14/022* (2013.01); *C04B 14/36* (2013.01); *C04B 41/009* (2013.01);
(Continued)

(58) Field of Classification Search
CPC ........ E04B 1/62; E04B 1/167; E04B 2103/02; E04C 2/04; C04B 14/022; C04B 14/36;
(Continued)

(56) References Cited

U.S. PATENT DOCUMENTS

2008/0245272 A1* 10/2008 Kucharski ............... C04B 24/00
106/638
2011/0027850 A1* 2/2011 Crawford ................ C04B 28/10
435/168

(Continued)

FOREIGN PATENT DOCUMENTS

WO    WO-2021070083 A1 *  4/2021    ............. B33Y 10/00
WO    WO-2022203639 A2 *  9/2022

OTHER PUBLICATIONS

Rothschild et al., Myco-Architecture Off Planet: Growing Surface Structures at Destination NIAC 2018 Phase I Final Report, 2019, obtained from https://ntrs.nasa.gov/api/citations/20190002580/downloads/20190002580.pdf (Year: 2019).*

(Continued)

*Primary Examiner* — Theodore V Adamos
(74) *Attorney, Agent, or Firm* — CANTOR COLBURN LLP

(57) ABSTRACT

A building structure comprising a first film and a second film. The first film and the second film are each impregnated with L-Dopa. The building structure further includes regolith bulk material between the first film and the second film.

20 Claims, 2 Drawing Sheets

(51) Int. Cl.

| | | |
|---|---|---|
| C04B 14/36 | (2006.01) | |
| C04B 41/00 | (2006.01) | |
| C04B 41/46 | (2006.01) | |
| C04B 41/50 | (2006.01) | |
| C04B 41/52 | (2006.01) | |
| C09J 4/06 | (2006.01) | |
| C09J 5/00 | (2006.01) | |
| C12N 1/20 | (2006.01) | |
| C12N 15/09 | (2006.01) | |
| C12P 13/04 | (2006.01) | |
| C12R 1/125 | (2006.01) | |
| E04B 1/16 | (2006.01) | |
| E04C 2/04 | (2006.01) | |

(52) U.S. Cl.
CPC .......... *C04B 41/46* (2013.01); *C04B 41/5001* (2013.01); *C04B 41/524* (2013.01); *C09J 4/06* (2013.01); *C09J 5/00* (2013.01); *C12N 1/205* (2021.05); *C12N 15/09* (2013.01); *C12P 13/04* (2013.01); *E04B 1/167* (2013.01); *E04C 2/04* (2013.01); *C12R 2001/125* (2021.05); *E04B 2103/02* (2013.01)

(58) Field of Classification Search
CPC ... C04B 41/09; C04B 41/5001; C04B 41/524; C04B 41/46; C09J 4/06; C09J 5/00; C12N 1/205; C12N 15/09; C12P 13/04; C12R 2001/125

See application file for complete search history.

(56) References Cited

U.S. PATENT DOCUMENTS

| | | | | |
|---|---|---|---|---|
| 2013/0125481 | A1* | 5/2013 | Marshall | E04B 1/62 52/169.14 |
| 2016/0090328 | A1* | 3/2016 | Wiktor | C04B 41/52 106/656 |
| 2016/0362334 | A1* | 12/2016 | Dosier | C04B 24/12 |
| 2018/0118623 | A1* | 5/2018 | Smith | C12N 3/00 |
| 2019/0106717 | A1* | 4/2019 | Dosier | C04B 22/0026 |
| 2020/0130871 | A1* | 4/2020 | Drexler | G21H 7/00 |

OTHER PUBLICATIONS

ASTM C114, American Society for Testing and Materials, Standard Test Methods for Chemical Analysis of Hydraulic Cement. Annual Book of ASTM Standards, Pennsylvania: ASTM International (May 2018).

ASTM C1365, American Society for Testing and Materials, Standard Test Method for Determination of the Proportion of Phases in Portland Cement and Portland-Cement Clinker Using X-Ray Powder Diffraction Analysis. Annual Book of ASTM Standards, Pennsylvania:ASTM International(2018).

ASTM C143, American Society for Testing and Materials, Standard Test Method for Slump of Hydraulic-Cement Concrete, Annual Book of ASTM Standards, Pennsylvania: ASTM International(2020).

ASTM C39, American Society for Testing and Materials, Standard Test Method for Compressive Strength of cylindrical Concrete Specimens. Annual Book of ASTM Standards, Pennsylvania: ASTM International(2021).

ASTM C403, American Society for Testing and Materials Standard Test Method for Time of Setting of Concrete Mixtures by Penetration Resistance. Annual Book of ASTM Standards, Pennsylvania: ASTM International(2017).

ASTM C469, American Society for Testing and Materials, Standard Test Method for Static Modulus of Elasticity and Poisson's Ratio of Concrete in Compression. Annual Book of ASTM Standards, Pennsylvania: ASTM International (2014).

ASTM C531, American Society for Testing and Materials, Standard Test Method for Linear Shrinkage and Coefficient of Thermal Expansion of Chemical-Resistant Mortars, Grouts, Monolithic Surfacings, and Polymer Concretes, Annual Book of ASTM Standards, Pennsylvania: ASTM International(2018).

ASTM C78, American Society for Testing and Materials, Standard Test Method for Flexural Strength of Concrete (Using Simple Beam with Third-Point Loading). Annual Book of ASTM Standards, Pennsylvania: ASTM International (2021).

ASTM D8337_D8337M, American Society for Testing and Materials Standard Test Method for Evaluation of Bond Properties of FRP Composite Applied to Concrete Substrate using Single-Lap Shear Test. Annual Book of ASTM Standards, Pennsylvania: ASTM International(2021).

Fordjour et al., "Metabolic engineering of *Escherichia coli* BL21 (DE3) for de novo production of L-DOPA from D-glucose", Microb Cell Fact Apr. 25, 2019;18(1):74. doi: 10.1186/s12934-019-1122-0. PMID: 31023316; PMCID: PMC6482505.

Haugen et al., "Nano-CT as tool for characterization of dental resin composites", Scientific reports, 10(1), 1-12 (2020).

Horiguchi et al., "Study on Lunar Cement Production Using Hokkaido Anorthite and Hokkaido Space Development Activities", Proceedings: 5th International Conf. on Space, 1996.

Wu et al., "Machine learning-assisted directed protein evolution with combinatorial libraries", Proceedings of the National Academy of Sciences, Apr. 2019, 116 (18) 8852-8858; DOI:10.1073/pnas. 1901979116.

Xu et al., "Unraveling the specific regulation of the shikimate pathway for tyrosine accumulation in Bacillus licheniformis", Journal of Industrial Microbiology & Biotechnology Aug. 2019; 46(8):1047-1059. doi: 10.1007/s10295-019-02213-2. Epub Jul. 11, 2019. PMID: 31297713.

* cited by examiner

MICROBES FOR SPACE STRUCTURES

CROSS-REFERENCE TO RELATED APPLICATION

This application is a U.S. nonprovisional patent application which claims priority to U.S. Provisional Patent Application No. 63/162,794, filed Mar. 18, 2021, which is incorporated by reference herein in its entirety.

BACKGROUND

The present disclosure relates to forming extraterrestrial structures, and, in particular, utilizing microbes to form extraterrestrial structures.

Building structure on the moon or other extraterrestrial locations, such as on the moon, can present challenges. Utilizing "concrete," such as lunar concrete, is one approach for creating large structures on the moon and other extraterrestrial surfaces. Lunar concrete includes aggregate (i.e., regolith), water, and cement, which is the binder. Regolith includes a mixture of powdery dust and rock present on an extraterrestrial surface. For example, lunar regolith is regolith on the surface of the moon. Typical methods for forming lunar concreate require transporting water and binder such as epoxy into space, which is costly and burdensome.

SUMMARY

According to one or more embodiments, systems and method are disclosed that can be used to form extraterrestrial (e.g., lunar) structures. In some non-limiting embodiments, a building structure comprising a first film and a second film. The first film and the second film are each impregnated with L-Dopa. The building structure further includes regolith bulk material between the first film and the second film.

In other embodiments, a method of fabricating a building component includes impregnating a first film and a second film with bacteria and regolith to form a first impregnated film and a second impregnated film. The bacteria are genetically engineered to produce a bioadhesive. The method further includes stacking the first impregnated film on the second impregnated film. The method also includes flowing, under a vacuum, regolith between the first impregnated film and the second impregnated film to form a composite part.

In some embodiments, a method of fabricating a building component includes impregnating a first film and a second film with a bacteria and regolith to form a first impregnated film and a second impregnated film. The bacteria form L-Dopa. The method also includes exposing the first impregnated film and the second impregnated film to heat and stacking the first impregnated film on the second impregnated film. The method further includes flowing, under a vacuum, regolith between the first impregnated film and the second impregnated film to form a composite part.

Additional features and advantages are realized through the techniques of the present disclosure. Other embodiments and aspects of the disclosure are described in detail herein and are considered a part of the claimed disclosure. For a better understanding of the disclosure with the advantages and the features, refer to the description and to the drawings.

BRIEF DESCRIPTION OF THE SEVERAL VIEWS OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Current methods for using regolith as a concretion produce parts and structures that are hard but not resistive to bending over long lengths or accurately shaped. Accordingly, described herein are methods, systems, and structures that use regolith as a feed stock to produce a binder, as well as a bulk material. The fabricated reinforced composites materials are hard, resistive to bending, and accurate in intended shape. The methods form extraterrestrial structures with minimal transportation costs.

Embodiments herein create a minimal microbial chassis, e.g., building material, that is easy to engineer and highly survivable under harsh conditions.

Embodiments further reduce the transportation requirements for forming extraterrestrial composites by shipping, instead of a complete component, thin ply films and bacteria. All other materials needed for construction will be available harvested from the lunar surface.

Other embodiments are methods of fabricating vacuum resin infused composite parts on an extraterrestrial surface, such as a lunar surface. The methods include, in some embodiments, combining bacterially formed L-Dopa with lunar regolith to form concretion, along with thin ply carbon fiber films. For high-strength composite parts in particular, a composite part can be formed using the regolith infused with L-Dopa, produced on the extraterrestrial surface via genetically engineered bacteria, as a bulk material to create composite beams that rely on the thin ply carbon to provide tensile strength.

The methods, systems, and structures described herein are extraterrestrial in some embodiments. As used herein, "extraterrestrial" means outside the Earth's atmosphere and includes the moon (lunar surfaces) and other planets, such as Venus and Mars.

Figure 1:
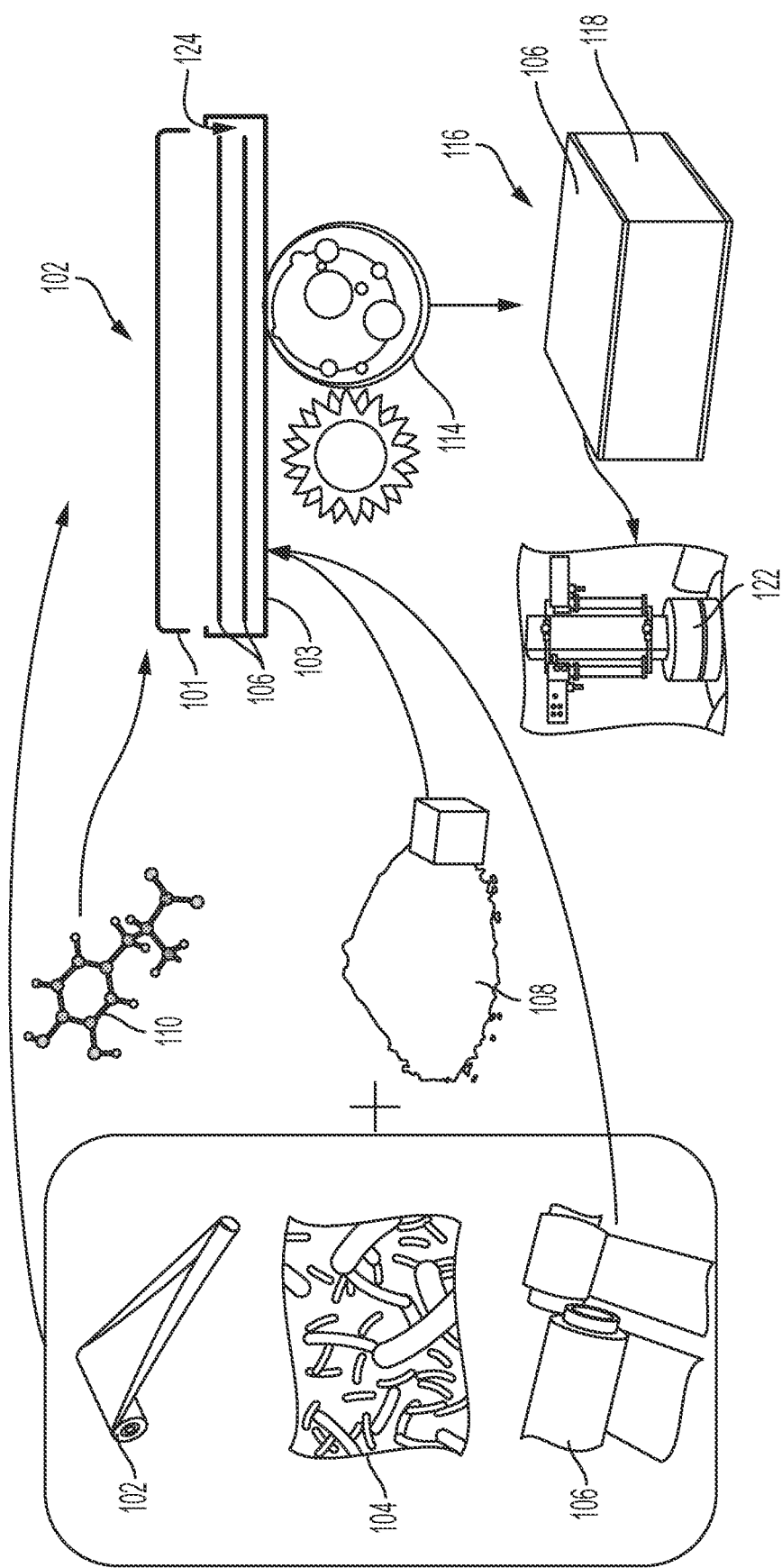
FIG. 1 is a pictorial representation illustrating methods of fabricating a building structure.

In one or more embodiments, and with reference to FIG. 1, a method of fabricating an extraterrestrial structure using deployable multi-part tooling is illustrated. Bacteria 104 are genetically engineered to produce a bioadhesive, e.g., L-Dopa 110. The bacteria 104 are genetically engineered strains capable of producing the bioadhesive, e.g., L-Dopa 110.

L-Dopa is also called levodopa or L-3,4-dihydroxyphenylalanine and has the following structure:

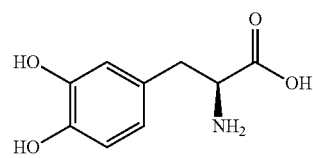 [SMILES: N[C@@H](Cc1ccc(O)c(O)c1)C(=O)O]

Although L-Dopa is used as a bioadhesive example, in other embodiments, the bacteria are genetically engineered to produce another bioadhesive. Embodiments of the disclosure are not limited to L-Dopa.

In one or more embodiments, *Bacillus subtilis* is the bacterial strain that is genetically engineered to form L-Dopa. *B. subtilis* is a physiologically and metabolically well-characterized, and tools to genetically manipulate the organism are available. *Bacillus subtilis* possess the ability to form spores, which allows them to survive for long periods under extremely harsh conditions and still readily produce the desired product once the proper conditions are established. This heartiness makes *B. subtilis* suitable for producing L-Dopa under a variety of conditions, including those on the lunar surface and other extraterrestrial surfaces.

In one or more embodiments, the bacteria 104 are genetically engineered to have certain enhancements using lunar regolith as an initial environment. For example, machine learning techniques can be used to optimize a bacterial strain for biomanufacturing and determine how best to make use of the available components of the regolith 108 for bacterial growth and production of the L-Dopa 110 in high yield and under a variety of conditions, or under specified conditions, such as those on the moon. Modeling is used to optimize the bacterial metabolism to utilize available nutrients to decrease the logistical requirements of transporting bacterial media into space, which can enable the bacteria to extract and make use of any present carbon, nitrogen, and phosphorus sources, as well as cofactors and other necessary elements that are present in the regolith. In some embodiments, competing metabolic pathways in the bacteria 104 are reduced or eliminated, and the bacterial strain is optimized to produce only L-tyrosine and the necessary enzymes for conversion to L-Dopa 110. These metabolic models can be used to identify a minimal media that can supplement the bacteria 104 with any remaining components that are not available in the extraterrestrial environment, e.g., the surface of the moon. The models and chassis developed during this research are adaptable to a variety of extreme conditions—arctic or desert regions, or even the surface of planets.

The bacteria 104 is combined with regolith 108, such as lunar regolith, which the bacteria 104 use as a feedstock to produce L-Dopa 110, as described below, on the surface of the carrier film 106. The regolith 108 is aggregate including dust and rock present on an extraterrestrial surface. For example, lunar regolith is regolith on the surface of the moon. The regolith 108 includes, for example, carbon, silica, or a combination thereof, along with other elements or compounds.

The regolith 108 also provides bulk when mixed with L-Dopa 110 formed by the bacteria 104, and the L-Dopa 110 acts as adhesive for the regolith 108, forming the bulk material.

Thin-ply carrier films 106 are impregnated with the bacteria 104, regolith 108, and optionally, additional feedstock (elements or compounds needed by the bacteria 104 to produce L-Dopa 110). The thin-ply carrier films 106 provide tensile strength to the final composite material.

In some embodiments, one, two, or more layers of the carrier films 106 are used to form the composite structure 116. In embodiments, the composite structure 116 includes two film layers, a first film layer and a second film layer, each on opposing surfaces of the composite structure 116.

In one or more embodiments, one or more of the thin-ply carrier films 106 are carbon composite films. In some embodiments, the carbon composite films are carbon fiber reinforced carbon films. In one or more embodiments, the thin-ply carrier films 106 have thicknesses about 10 to about 100 mil (about 0.254 to about 2.54 millimeters).

In one or more embodiments, the bacteria 104 and regolith 108 are impregnated, for example by injection, into the thin-ply carrier films. The impregnation is conducted on the extraterrestrial surface, e.g., the lunar surface.

In embodiments, where two film layers are used to form the composite structure 116, the first film and the second film are each impregnated with the L-Dopa 110.

The L-Dopa formed by the bacteria 104 is combined with the regolith 108 which will be used to form the regolith bulk material 118 of the composite structure 116. The L-Dopa 110 is activated by exposure to heat, for example heat generated by solar-heated pressurized air during the lunar day, which induces the bacteria 104 to produce the L-Dopa.

At least two layers of carrier films 106 are stacked in deployable tooling 102 that includes an inflatable stricture such as a one-sided open mold 103 and a vacuum bag 101. The bulk material 118, which is regolith 108 combined with L-Dopa 110, is flowed into the deployable tooling 102 while applying a vacuum. In one or more embodiments, vacuum infusion centrifugal casting using controlled heat and vacuum are be used to accelerate bacterial metabolism. The composite structure 116 includes the regolith bulk material 118 between layers of carrier film 106 (first and second film layers).

In some embodiments, bacteria termination, i.e., production of L-Dopa 110, is achieved by exposing the composite structure 116 of reinforced carrier films 106 sandwiching bulk regolith 118 to ambient lunar conditions 114. The foregoing processes produce extraterrestrial structures, such as lunar building structures, on extraterrestrial surfaces.

The fabrication processes create accurately shaped as well as strong composite parts 116. In some embodiments, the composite part 116 is tested for tensile strength or other properties desired.

Figure 2:
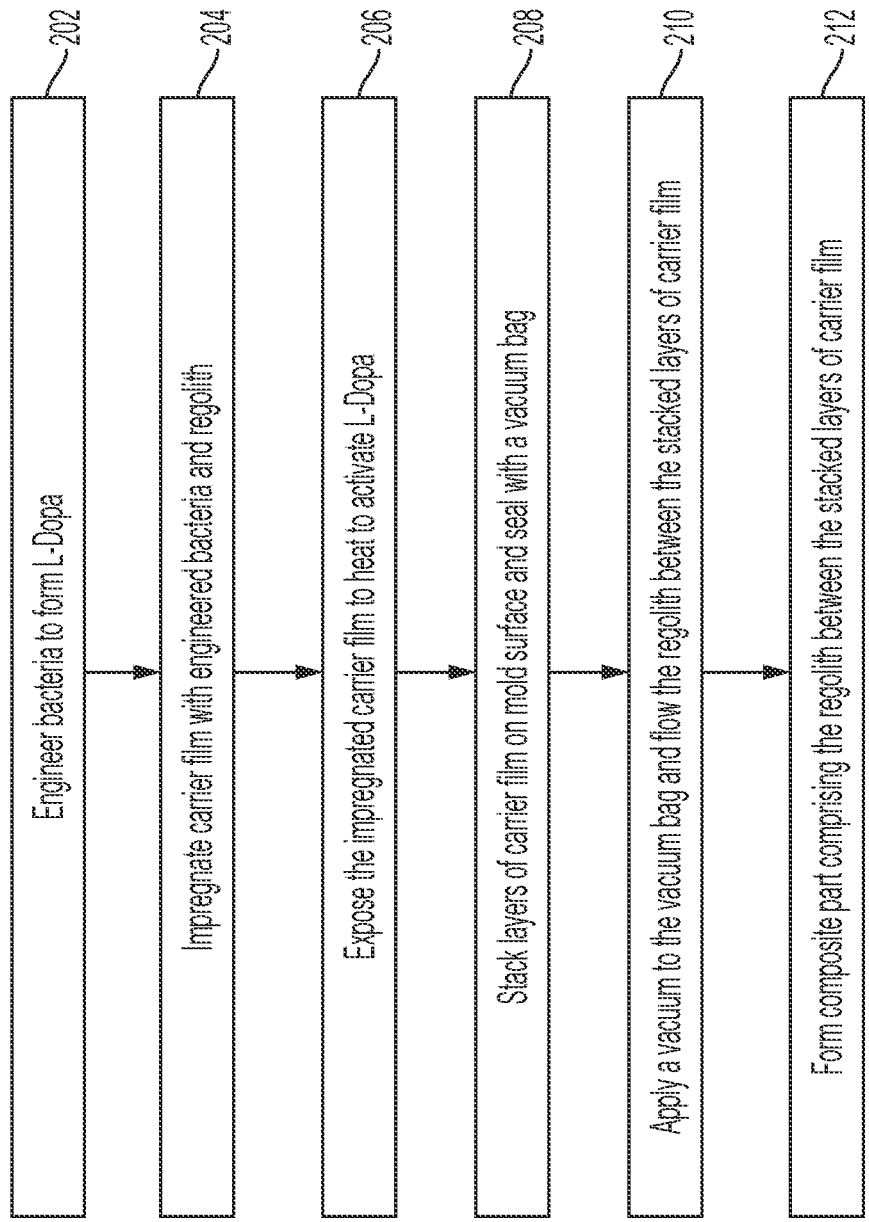
FIG. 2 is a flow chart describing methods of fabricating a building structure.

FIG. 2 illustrates a flow diagram of illustrating a method of fabricating a composite part according to embodiments. In box 202, the method includes engineering bacteria to form L-Dopa. In box 204, the method includes impregnating a carrier film with the engineered bacteria and regolith. In box 206, the method includes exposing the impregnated carrier film to heat to activate L-Dopa. In box 208, the method includes stacking layers of carrier film on a mold surface and sealing with a vacuum bag. In box 210, the method includes applying a vacuum to the vacuum bag and flowing the regolith between the stacked layers of carrier film. In box 212, the method includes forming the composite part comprising the regolith between the stacked layers of carrier film.

Flexible manufacturing in harsh environments with limited resources will allow the establishment and maintenance of capabilities in previously underutilized regions. Bacterial metabolic engineering presents a unique approach to enable manufacturing. Bacteria are able to utilize a wide variety of nutrient sources and rapidly adapt to environmental conditions. In addition, modern synthetic biology tools and metabolic engineering techniques allow researchers to modify bacterial chassis to optimize production, and in some cases create completely novel compounds. Bacterial manufacturing produces a natural amplification effect; each tiny microbe is a single factory that can produce a number of outputs, even as it divides and produces additional factories through the natural bacterial reproductive cycle.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A building structure comprising:
   a first film and a second film, the first film and the second film each impregnated with L-Dopa; and
   regolith bulk material between the first film and the second film.

2. The building structure of claim 1, wherein the regolith bulk material is lunar regolith bulk material.

3. The building structure of claim 1, wherein at least one of the first film and the second film is a carbon film.

4. The building structure of claim 1, wherein the first film and the second film are carbon composite films.

5. The building structure of claim 1, wherein the regolith bulk material comprises carbon, silica, or a combination thereof.

6. The building structure of claim 1, wherein the regolith bulk material further includes L-Dopa.

7. The building structure of claim 1, wherein the building structure is an extraterrestrial building structure.

8. A method of fabricating a building component, the method comprising:
   impregnating a first film and a second film with bacteria and regolith to form a first impregnated film and a second impregnated film, the bacteria being genetically engineered to produce a bioadhesive;
   stacking the first impregnated film on the second impregnated film; and
   flowing, under a vacuum, regolith between the first impregnated film and the second impregnated film to form a composite part.

9. The method of claim 8, wherein the regolith is lunar regolith.

10. The method of claim 8, wherein at least one of the first film and the second film is a carbon film.

11. The method of claim 8, wherein the first film and the second film are carbon composite films.

12. The method of claim 8, wherein the regolith comprises carbon, silica, or a combination thereof.

13. The method of claim 8, wherein the regolith flowed under the vacuum further includes L-Dopa.

14. The method of claim 8, further comprising exposing the first impregnated film and the second impregnated film to heat.

15. A method of fabricating a building component, the method comprising:

impregnating a first film and a second film with a bacteria and regolith to form a first impregnated film and a second impregnated film, the bacteria forming L-Dopa;

exposing the first impregnated film and the second impregnated film to heat;

stacking the first impregnated film on the second impregnated film; and flowing, under a vacuum, regolith between the first impregnated film and the second impregnated film to form a composite part.

16. The method of claim 15, wherein the regolith is lunar regolith.

17. The method of claim 15, wherein impregnating the first film and the second film is performed on a lunar surface.

18. The method of claim 15, wherein the first film and the second film are carbon composite films.

19. The method of claim 15, wherein the regolith comprises carbon, silica, or a combination thereof.

20. The method of claim 15, further comprising engineering the bacteria to form L-Dopa.

* * * * *